(12) United States Patent
Fan et al.

(10) Patent No.: US 9,649,265 B2
(45) Date of Patent: May 16, 2017

(54) LIQUID CLEANING COMPOSITION CONTAINING LONG-CHAIN FATTY ACID

(75) Inventors: Aixing Fan, Bridgewater, NJ (US); Jeffrey Mastrull, Middlesex, NJ (US); Edward Simpson, Sayreville, NJ (US)

(73) Assignee: Colgate-Palmolive Company, New York, NY (US)

( * ) Notice: Subject to any disclaimer, the term of this patent is extended or adjusted under 35 U.S.C. 154(b) by 498 days.

(21) Appl. No.: 13/992,748

(22) PCT Filed: Dec. 9, 2010

(86) PCT No.: PCT/US2010/059683
§ 371 (c)(1),
(2), (4) Date: Jun. 9, 2013

(87) PCT Pub. No.: WO2012/078160
PCT Pub. Date: Jun. 14, 2012

(65) Prior Publication Data
US 2013/0255710 A1 Oct. 3, 2013

(51) Int. Cl.
| | | |
|---|---|---|
| *C08F 226/02* | (2006.01) |
| *A61P 3/06* | (2006.01) |
| *A61K 31/785* | (2006.01) |
| *A61K 8/36* | (2006.01) |
| *A61K 8/44* | (2006.01) |
| *A61K 8/46* | (2006.01) |
| *A61K 8/60* | (2006.01) |
| *A61Q 5/02* | (2006.01) |
| *A61Q 5/12* | (2006.01) |
| *A61Q 19/10* | (2006.01) |

(52) U.S. Cl.
CPC ............... *A61K 8/361* (2013.01); *A61K 8/44* (2013.01); *A61K 8/463* (2013.01); *A61K 8/604* (2013.01); *A61Q 5/02* (2013.01); *A61Q 5/12* (2013.01); *A61Q 19/10* (2013.01)

(58) Field of Classification Search
CPC .......... A61K 8/361; A61K 8/44; A61K 8/463; A61K 8/604; A61Q 5/02; A61Q 5/12; A61Q 9/10
See application file for complete search history.

(56) References Cited

U.S. PATENT DOCUMENTS

| | | | |
|---|---|---|---|
| 3,929,678 A | 12/1975 | Laughlin et al. | |
| 4,209,449 A | 6/1980 | Mayhew et al. | |
| 4,565,647 A * | 1/1986 | Llenado ............ | 516/14 |
| 5,104,643 A | 4/1992 | Grollier et al. | |
| 5,132,037 A | 7/1992 | Greene et al. | |
| 5,147,574 A | 9/1992 | MacGilp et al. | |
| 5,607,678 A | 3/1997 | Moore et al. | |
| 5,632,978 A | 5/1997 | Moore et al. | |
| 5,670,471 A | 9/1997 | Amalric et al. | |
| 5,683,972 A | 11/1997 | Zocchi | |
| 5,908,617 A | 6/1999 | Moore et al. | |
| 5,929,024 A | 7/1999 | Stringer et al. | |
| 5,952,286 A * | 9/1999 | Puvvada et al. ............. | 510/417 |
| 5,994,280 A | 11/1999 | Giret et al. | |
| 6,077,816 A | 6/2000 | Puvvada et al. | |
| 6,087,320 A | 7/2000 | Urfer et al. | |
| 6,191,188 B1 | 2/2001 | Hossel et al. | |
| 6,776,995 B1 | 8/2004 | Revivo | |
| 6,906,016 B1 | 6/2005 | Tsaur | |
| 6,977,082 B2 | 12/2005 | Seitz, Jr. et al. | |
| 7,704,932 B2 | 4/2010 | Evans et al. | |
| 2003/0083210 A1 | 5/2003 | Goldberg et al. | |
| 2005/0136026 A1 | 6/2005 | Qiu et al. | |
| 2006/0141014 A1 | 6/2006 | Eknoian et al. | |
| 2007/0032393 A1 | 2/2007 | Patel et al. | |
| 2008/0153727 A1 | 6/2008 | Tsaur et al. | |
| 2008/0153729 A1 | 6/2008 | Tsaur et al. | |
| 2008/0153730 A1 | 6/2008 | Tsaur et al. | |
| 2009/0156450 A1 | 6/2009 | Tsaur | |
| 2010/0062961 A1 | 3/2010 | Post et al. | |
| 2010/0075881 A1 | 3/2010 | Tsaur | |

FOREIGN PATENT DOCUMENTS

| | | |
|---|---|---|
| DE | 19814608 | 9/1999 |
| EP | 0355368 | 2/1994 |
| EP | 1718268 | 1/2008 |
| EP | 1994922 | 11/2008 |
| WO | WO 93/25650 | 12/1993 |
| WO | WO 94/17166 | 8/1994 |
| WO | WO 97/05857 | 2/1997 |
| WO | WO 2009/030594 | 3/2009 |
| WO | WO 2009/100262 | 8/2009 |

(Continued)

OTHER PUBLICATIONS

Cognis Corporation, "Luscious Whipped Facial Cleansing Cream," retrieved from internet Oct. 13, 2010.
Cognis Corporation, "Plantaren® 2000 N Up" Product Data Sheet retrieved from internet 2013.
Colgate-Palmolive Co., MSDS for "Softsoap Body Wash, Pure Cashmere", http://householdproducts.nlm.nih.gov/cgi-bin/household/brands?tbl=brands&id=3008073 (MSDS Date: Jan. 2, 2008).
International Search Report and Written Opinion in International Application No. PCT/US10/059676, mailed Oct. 27, 2011.
International Search Report and Written Opinion in International Application No. PCT/US10/059683, mailed Oct. 27, 2011.
Proctor & Gamble Co., MSDS for "Olay Moisturizing Body Wash-Old Product", http://householdproducts.nlm.nih.gov/cgi-bin/household/brands?tbl=brands&id=16003086 (MSDS Date Apr. 1, 2000).
Thareja et al., 2011, "Development of an in situ rheological method to characterize fatty acid crystallization in complex fluids," Colloids & Surfaces A: Physiochemistry 388:12-20.
Unilever, MSDS for "Dove Sensitive Skin Moisturizing Body Wash, New", http://householdproducts.nlm.nih.gov/cgi-bin/household/brands?tbl=brands&id=12002018 (MSDS Date Oct. 21, 1997).

(Continued)

*Primary Examiner* — Suzanne Ziska
*Assistant Examiner* — Thurman Wheeler

(57) ABSTRACT

An aqueous composition includes: (a) surfactants comprising a salt of a $C_{10-16}$ alcohol ethoxylate sulfate, a betaine surfactant, and an alkyl polyglucoside, wherein the salt of the $C_{10-16}$ alcohol ethoxylate sulfate is present in a quantity that is greater than any other surfactant; (b) at least 15 weight % of the composition of a $C_{12-18}$ fatty acid. A cleansing method includes applying the composition to skin or hair and washing, and optionally rinsing with water.

8 Claims, 2 Drawing Sheets

(56) References Cited

FOREIGN PATENT DOCUMENTS

| | | |
|---|---|---|
| WO | WO 2009/100276 | 8/2009 |
| WO | WO 2010/025898 | 3/2010 |

OTHER PUBLICATIONS

Unilever, MSDS for "Dove Ultra Moisturizing Body Wash", http://householdproducts.nlm.nih.gov/cgi-bin/household/brands?tbl=brands&id=12002005 (MSDS Date Aug. 2, 1995).
Unilever, 2010, "Whipped Souffle Blackberry Cream Body Wash." Mintel GNPD Accession No. 1328265.
Written Opinion in International Application No. PCT/US10/059676, mailed Nov. 20, 2012.
Written Opinion in International Application No. PCT/US10/059683, mailed Nov. 20, 2012.

\* cited by examiner

LIQUID CLEANING COMPOSITION CONTAINING LONG-CHAIN FATTY ACID

BACKGROUND

Shower gels, body washes, cleansing lotions, liquid soaps, and the like (hereinafter collectively referred to as "liquid cleaning compositions" be they liquids, gels, lotions or foams) have grown increasingly popular in recent times. Such compositions typically comprise a mixture of surfactants as skin cleaning agents. The performance of these compositions can be modified by modifying the interaction of the surfactants in the mixed surfactant system.

It is known to use salts to modify the packing of surfactants to achieve higher viscosity. See, e.g., Lin et al., "Spherical-To-Wormlike Micelle Transition In CTAB Solutions", J. Phys. Chem., 1994, 98, 5984-5993 and Yang, "Viscoelastic wormlike micelles and their applications", Current Opinion in Colloid & Interface Science 7 (2002) 276-281. With the addition of increasing concentrations of salt, the viscosity typically increases, reaches a maximum, and suddenly decreases. This observation is related to the formation of dense wormlike micelles (tighter packing which results in high viscosities) and then branched wormlike micelles (which causes the viscosity to drop).

However, high levels of salt cause the cleaning product to be stringy, and adversely affect the foam properties of the product.

It is therefore desired to increase the viscosity of liquid cleaning compositions and to create different compositional forms.

SUMMARY

An aqueous composition comprising: a) surfactants comprising a salt of a $C_{10-16}$ alcohol ethoxylate sulfate, a betaine surfactant, and an alkyl polyglucoside, wherein the salt of the $C_{10-16}$ alcohol ethoxylate sulfate is present in a quantity that is greater than any other surfactant; and b) at least 15 weight % of the composition of a $C_{12-18}$ fatty acid. The composition has a crystalline visual appearance.

Also a cleansing method comprising applying the composition to skin or hair and washing, and optionally rinsing with water.

DETAILED DESCRIPTION

Figure 1:
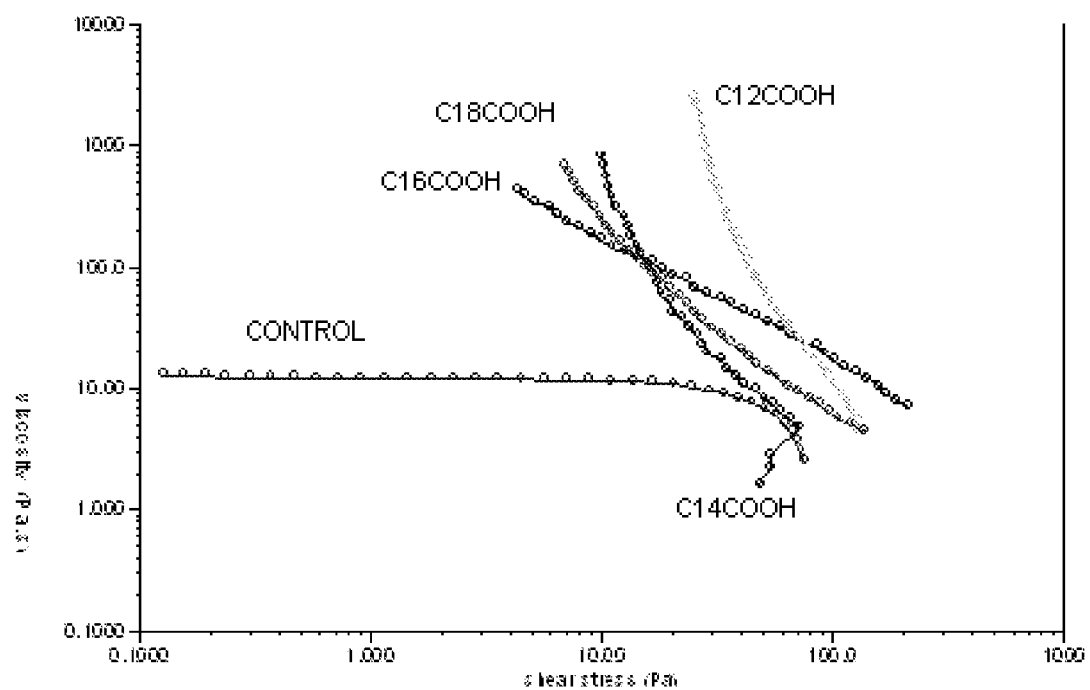
FIG. 1 is a rheology profile of high level of fatty acid additives in a cleaning composition.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight based on the weight of the composition. The amounts given are based on the active weight of the material.

The composition is particularly well-suited for use as a liquid cleaning composition for personal care, but is also suitable for use as a disinfectant, surgical scrub, hospital hand wash product, hand sanitizer gel, wound care agent, and the like. Use of the composition on inanimate objects (e.g., as a hard surface cleaner) is also possible.

Surfactants

The composition includes surfactants comprising a salt of a $C_{10-16}$ alcohol ethoxylate sulfate, a betaine surfactant, and an alkyl polyglucoside.

In certain embodiments, the combined amount of surfactants are present in an amount of at least 5, 6, 7, 8, 9, 10, 11, 12, or 13 weight % of the composition.

The salt of a $C_{10-16}$ alcohol ethoxylate sulfate can be selected to any one or more of the salt of a $C_{10-16}$ alcohol ethoxylate sulfates. In certain embodiments, the $C_{10-16}$ is lauryl. The average moles of ethylene oxide can be 1-30. Typically, there is an average of 1 to 3 moles of ethylene oxide. The cation for the salt can be any of the typical salt cations, such as sodium, ammonium, alkali metal, alkaline earth metal, triethanolamine, or others. In certain embodiments, sodium is selected.

In certain embodiments, the salt of the $C_{10-16}$ alcohol ethoxylate sulfate comprises sodium lauryl ether sulfate. In certain embodiments, the salt of the $C_{10-16}$ alcohol ethoxylate sulfate comprises sodium lauryl ether sulfate with an average of 2 moles of ethylene oxide. In certain embodiments, the salt of the $C_{10-16}$ alcohol ethoxylate sulfate is present in a quantity that is greater than any other surfactant.

Examples of betaine surfactants include, but are not limited to, one or combinations of cocodimethylcarboxymethylbetaine, cocamidopropylbetaine, lauryldimethylcarboxymethyl-betaine, lauryldimethylcarboxyethylbetaine, cetyldimethylcarboxymethylbetaine, lauryl-bis-(2-hydroxyethyl)carboxymethylbetaine, oleyldimethylgammacarboxypropylbetaine, and lauryl-bis-(2-hydroxypropyl)-carboxyethylbetaine. In certain embodiments, the betaine surfactant comprises cocamidopropyl betaine.

The alkyl in the alkyl polyglucoside can be any alkyl or combinations thereof, such as decyl, lauryl, or coco. In certain embodiments, the alkyl polyglucoside comprises decyl glucoside.

In certain embodiments, the surfactants comprise, based on a total weight of the surfactants, 60-70 weight % of the salt of a $C_{10-16}$ alcohol ethoxylate sulfate, 20-30 weight % betaine surfactant, and 5-15 weight % alkyl polyglucoside.

In certain embodiments, the surfactants comprise, based on the weight of the surfactants, 66 to 67, or about 66.4, weight % of the salt of a $C_{10-16}$ alcohol ethoxylate sulfate, 24 to 25, or about 24.4, weight % betaine surfactant, and 9 to 10, or about 9.2, weight % alkyl polyglucoside.

Additional surfactants can be included in the composition. Examples of additional surfactants are listed in McCutcheon's Emulsifiers and Detergents, 1993 Annuals, (hereafter McCutcheon's), McCutcheon Division, MC Publishing Co., Glen Rock, N.J.

Fatty Acid

The composition comprises at least one $C_{12}$-$C_{18}$ fatty acid, preferably a $C_{16}$-$C_{18}$ fatty acid. Specific suitable fatty acids include but are not limited to lauric acid, myristic acid, palmitic acid and stearic acid. The composition can comprise a single type of fatty acid or more than one type of fatty acid. In certain embodiments, $C_{16}$-$C_{18}$ fatty acids are preferred because $C_{12}$-$C_{14}$ fatty acids can reduce the amount of foam that is generated.

The composition preferably comprises the fatty acid in an amount of 15 to 30 wt. %, or 15 wt. % to 25 wt. %, based on a weight of the composition.

Crystalline foams have a crystalline, whipped cream like appearance. The crystals have an average size greater than 50 microns or greater than 100 microns or greater than 200 microns, as determined by polarized light microscopy.

The crystals provide the foam with excellent stability. In preferred embodiments, the foams have a drainage time greater than 100 seconds or greater than 200 seconds or 100-450 seconds.

Moreover, crystalline foams can assume and retain the shape of the dispenser nozzle in certain embodiments.

Carrier

The carrier of the composition comprises water, which is preferably demineralized water and/or softened water.

Skin Care Agent

In certain embodiments, compositions can contain 0% to about 5%, and preferably 0.1% to about 3%, by weight, of a skin care agent.

The identity of the skin care agent is not particularly limited, as long as the agent does not adversely affect the stability or efficacy of the composition. One important class of skin care agents is emollients. Emollients are cosmetic ingredients that help to maintain a soft, smooth, and pliable skin appearance. Emollients function by remaining on the skin surface or in the stratum corneum to act as lubricants, to reduce flaking, and to improve skin appearance.

In general, the skin care agent includes polymers (e.g., polyvinylpyrrolidine), protein derivatives (e.g., derivatized hydrolyzed wheat protein), ethoxylated fatty ethers, cellulosics (e.g., hydroxyethylcellulose), and similar skin care agents. For example, suitable skin care agents include, but are not limited to, esters comprising an aliphatic alcohol having 2 to about 18 carbon atoms condensed with an aliphatic or aromatic carboxylic acid including 8 to about 20 carbon atoms, e.g., isopropyl myristate, decyl oleate, and cetearyl isononanate. The ester is either straight chained or branched. Preferably, the ester has a molecular weight of less than about 500 and provides emollient properties.

Non-limiting examples of other skin care agents include, but are not limited to, polyvinyl-pyrrolidone, polyquaternium-4, polyquaternium-7, polyquaternium-10, guar gum derivatives, hydroxypropylmethylcellulose, hydroxyethylcellulose, a polyethylene glycol, a methyl ether of a polyethylene glycol, quaternium-79, wheat germamidopropyl hydroxypropyl dimonium hydrolyzed wheat protein, stearyl methicone, dimethicone copolyol, dimethicone propyl PG betaine, poly(sodium styrene sulfonate), sorbitan oleate, steareth-2, steareth-21, isoceteth-20, PEG-7 glyceryl cocoate, PEG-75 lanolin, glycereth-26, PPG-5-ceteth-20, a $C_{12}$-$C_{20}$ alcohol, canola oil, glyceryl laurate, triglyceryl monostearate, glyceryl monostearate, vitamin E acetate, sunflower seed amidopropylethyldimonium ethylsulfate, sodium PEG-7 olive oil carboxylate, PPG-1 hydroxyethyl caprylamide, PPG-2 hydroxyethyl cocamide, mineral oil, petrolatum, aloe barbadensis, isostearamidopropylmorpholine lactate, strontium acetate, and palmitamidopropyltrimonium chloride. The above skin care agents can be used alone or in admixture.

Additional Optional Ingredients

The composition also can contain additional optional ingredients well known to persons skilled in the art, such as dyes and fragrances, that are present in a sufficient amount to perform their intended function and do not adversely affect the cleaning efficacy of the composition. Such optional ingredients typically are present, individually, from 0% to about 5%, by weight, of the composition, and, collectively, from 0% to about 20%, by weight, of the composition.

Classes of optional ingredients include, but are not limited to, dyes, fragrances, pH adjusters, preservatives, thickeners, viscosity modifiers, buffering agents, antioxidants, foam enhancers, chelating agents, opacifiers, hydric solvents, hydrotropes, humectants, antimicrobials (see, e.g., U.S. Pat. No. 6,977,082) and similar classes of optional ingredients known to persons skilled in the art.

Specific classes of optional ingredients include alkanolamides as foam boosters; parabens as preservatives; inorganic phosphates, sulfates, and carbonates as buffering agents; EDTA and phosphates as chelating agents; and acids and bases as pH adjusters.

Examples of basic pH adjusters are ammonia; mono-, di-, and tri-alkyl amines; mono-, di-, and tri-alkanolamines; alkali metal and alkaline earth metal hydroxides; and mixtures thereof. However, the identity of the basic pH adjuster is not limited, and any basic pH adjuster known in the art can be used. Specific, nonlimiting examples of basic pH adjusters are ammonia; sodium, potassium, and lithium hydroxide; monoethanolamine; triethylamine; isopropanolamine; diethanolamine; and triethanolamine.

Examples of acidic pH adjusters are the mineral acids and polycarboxylic acids. Nonlimiting examples of mineral acids are hydrochloric acid, nitric acid, phosphoric acid, and sulfuric acid. Nonlimiting examples of polycarboxylic acids are citric acid, glycolic acid, and lactic acid. The identity of the acidic pH adjuster is not limited and any acidic pH adjuster known in the art, alone or in combination, can be used.

In certain embodiments, the composition is free of inorganic salts, such as sodium chloride. In certain other embodiments, the amount of sodium chloride (and/or all inorganic salts) in the composition is limited to 1 wt. % or less.

An alkanolamide to provide foam enhancement can be, but is not limited to, cocamide MEA, cocamide DEA, soyamide DEA, lauramide DEA, oleamide MIPA, stearamide MEA, myristamide MEA, lauramide MEA, capramide DEA, ricinoleamide DEA, myristamide DEA, stearamide DEA, oleylamide DEA, tallowamide DEA, lauramide MIPA, tallowamide MEA, isostearamide DEA, isostearamide MEA, and mixtures thereof.

The composition also can contain a preservative in an amount of 0-5 wt. % or 0.01-1 wt. %. Examples of preservatives include, but are not limited to, sorbic acid, potassium sorbate, the parabens (like benzylparaben), imidazolinylurea, methylchloroisothiazolinone, and the hydantoins, like DMDM hydantoin. Additional preservatives as disclosed in the CTFA Handbook at page 78.

The composition can contain an antioxidant and/or an ultra-violet light (UV) absorber, each independently in an amount of 0% to about 0.5% by weight. Examples of antioxidants and UV absorbers include, but are not limited to, BHA, BHT, sodium ascorbate, potassium sulfite, erythorbic acid, benzophenone-1 through benzophenone-12, and PABA. Additional antioxidants and UV absorbers can be found in the CTFA Handbook at pages 78 and 98.

The composition can have a pH that is typical of a skin cleanser, which is usually about 4 to about 9. In certain embodiments, the composition has a pH of 5 to 8, 6 to 8, or 6.5 to 7.5.

The composition can optionally contain humectants. Nonlimiting examples of humectants, include, but are not limited to, ascorbic acid, ascorbyl dipalmitate, acetamide MEA, glucose glutamate, glucuronic acid, TEA-lactate, TEA-PCA, corn syrup, fructose, glucose, glycerin, glycol, 1,2,6-hexanetriol, sodium lactate, sodium PCA, hydrogenated starch hydrolysate, inositol, lactic acid, lactose, mannitol, PCA, PEG-10 propylene glycol, polyamino sugar condensate, propylene glycol, pyridoxine dilaurate, saccharide hydrolysate, hydroxystearyl methylglucamine, glucamine, maltitol, mannitol, methyl gluceth-10, methyl gluceth-20, riboflavin, PEG-4, PEG-6, PEG-8, PEG-9, PEG-10, PEG-12, PEG-14, PEG-16, PEG-18, PEG-20, PEG-32, PEG-40, glutamic acid, glycereth-7, glycereth-12, glycereth-26, saccharide isomerate, sorbeth-20, sorbitol, sucrose, thioglycerin, tris-(hydroxymethyl)nitromethane, tromethamine, histidine, PEG-75, PEG-135, PEG-150, PEG-200, PEG-5 pentaerythritol ether, polyglyceryl sorbitol, sorbitol, urea, xylitol, and mixtures thereof.

In certain embodiments, the method comprises applying the composition to the skin or hair, and optionally rinsing with water. In certain other embodiments, the method comprises dispensing the composition from the container in which it is stored.

SPECIFIC EMBODIMENTS

The invention is further described in the following examples. The examples are merely illustrative and do not in any way limit the scope of the invention as described and claimed.

Test Materials

| Tradename | INCI name | Supplier |
|---|---|---|
| Amphosol HCA | Cocamidopropryl betaine (CAP betaine) | Stepan |
| Steol CS-230 | Sodium lauryl ethoxylated sulfate (SLES) | Stepan |
| Emery 652 | Lauric Acid (C12) | Cognis Corporation |
| Emery 655 | Myristic Acid (C14) | Cognis Corporation |
| Pamitic acid | Palmitic Acid (C16) | KlC Chemicals, Inc. |
| Stearic acid | Stearic Acid (C18) | KlC Chemicals, Inc |

Rheology studies were carried out using a TA instrument AR2000 Rheometer with a 14 mm small vane geometry. A shear rate ramp was used to obtain the viscosity vs. shear stress response.

Light microscopy and imaging were accomplished using an Olympus BX61 motorized compound light microscope mounted with an Olympus DP70 color digital camera accompanied by Olympus/SIS Microsuite Five Software. Shower gel samples were prepared by applying a drop of product onto a glass slide and covering it with a glass coverslip. Samples were examined using the following transmitted light microscopical techniques: brightfield, phase contrast, differential interference contrast and polarized light under crossed polars. Magnification used was 100×.

DSC was measured using a TA instrument 2920 MDSC under a nitrogen atmosphere. About 10±5 mg of body wash sample was transferred into a hermetically sealed aluminum pan for DSC measurement. DSC curves were recorded between 10 and 100° C. at a heating and cooling rate of 5° C./min.

Foam Test Method

A foam shake tester (Gaum Incorporated, Robbinsville, N.J.) is used for the foam measurements. The procedure to measure foam quantity is detailed below. Artificial sebum used for the foaming study is made according to Spangler, W. G. et al, J Am Oil Chem Soc. 42, 723 (1965).

1 g of sebum, 15 g of 10% surfactant solution, and 84 g of 250 ppm hard water are weighed and delivered to a 250 ml beaker. The mixture is slowly heated to approximately 40.5° C. (105° F.) on a hot plate. Meanwhile, a 500 ml graduated cylinder with a magnetic bar inside is heated to approximately 40.5° C. (105° F.) by holding the cylinder under 40.5° C. (105° F.) running tap water. When the sample reached 40.5° C. (105° F.), it is transferred to the warm graduated cylinder; and 2-3 drops of dye solution are added.

The flash foam, a measure of the quickness of foam generation, is read after 4 rotations of the cylinder. (1 rotation is equal to one upside down/right side up motion of the cylinder).

The maximum foam and drainage time are recorded after another 12 rotations. Drainage time is measured by accurately recording the time it took for the liquid phase to come back to its original volume. Drainage refers to the process of outflow (efflux) of the solution from the foam layers. As a result of the drainage, the liquid content in the foam decreases and the foam films become thinner.

Comparative Example

A composition representative of conventional liquid cleaning compositions was prepared as a comparative example and as a base for the compositions of the invention. The comparative cleaning composition (hereinafter "CCC") is shown below.

| Ingredient Name | Weight % |
|---|---|
| Water and minors | Q.S. |
| C10-16 Alcohol Ethoxylate, Sulfated, Sodium Salt (SLES) | 8.67 |
| Cocamidopropyl Betaine | 3.17 |
| Alkyl Polyglycoside | 0.83 |
| Sodium Chloride | 0.53 |
| Lauryl Polyglucose | 0.36 |
| 1,3-Bis(Hydroxymethyl)-5,5-Dimethylhydantoin (DMDM Hydantoin) | 0.27 |
| Polyquaternium-7 | 0.21 |
| Tetrasodium EDTA | 0.08 |
| Total Materials | 100 |

Fatty acids can be added into CCC at different levels. High levels of fatty acids can turn the CCC from a non-structured viscous liquid into a structured, shear-thinning gel.

Example 1

High levels of fatty acid turned CCC from a non-structured viscous liquid into a structured, shear-thinning gel. The resulting product has a whipped cream type of appearance.

The shear viscosity of shower gel samples were investigated using a range of shear rates (D), from 0.01 to 30 sec$^{-1}$. Gels and non-structured viscous fluids can easily be distinguished by measuring their flow behavior. Structured fluids exhibit non-Newtonian behavior, while non-structured fluids do not.

FIG. 1 shows the rheological profiles of 15% fatty acids in CCC. The control is CCC with 1% NaCl. CCC (with no salt) cannot be directly used as a control because of its low viscosity (about 32.5 cps). C12 acid was the most effective thickener amongst the four fatty acids evaluated.

Example 2

A polarized microscopy image of 15% C16 fatty acid was prepared, and a polarized microscopy image was taken (not shown). When polarized light passes through anisotropic crystals it decomposes into two rays resulting in birefringence. The fatty acid product contains large anisotropic crystals. It has a crystalline, whipped cream appearance.

Example 3

The effect on drainage time for a C16 acid is evaluated. The results are shown in the table below.

| Composition | Flash Foam (mL) | Max Foam (mL) | Drainage Time (sec) |
|---|---|---|---|
| CCC (1% NaCl) | 283 | 427.5 | 57 |
| 5% C16 Acid + 95% CCC | 257.5 | 385 | 157.5 |
| 10% C16 Acid + 90% CCC | 237.5 | 370 | 142.5 |
| 13% C16 Acid + 87% CCC | — | — | about 150 |
| 14% C16 Acid + 86% CCC | — | — | about 150 |
| 15% C16 Acid + 85% CCC | 250 | 370 | 360 |

It can be seen that when at least 15 weight % fatty acid is used, the drainage time more than doubles. The drainage time up to 14 weight % is about constant at about 150 seconds, but the draining time increases to 360 seconds at 15 weight %. The increase in drainage time provides for a more stable foam over a longer period of time to provide a consumer with longer lasting foam.

Example 4

Figure 2:
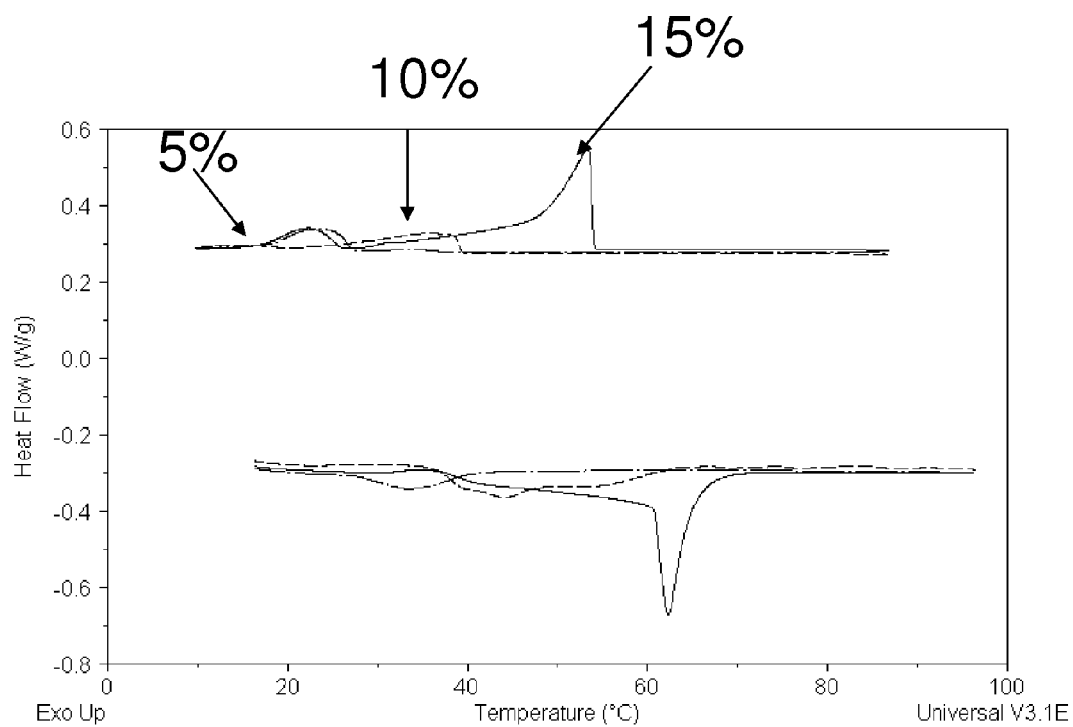
FIG. 2 are DSC profiles of a cleaning composition with 5, 10, and 15% C16 fatty acid.

To further understand how high levels of fatty acid stabilize foam, differential scanning calorimetry was used to study the behavior of CCC with progressively increasing levels of C16 acid. FIG. 2 shows the DSC plot where heat flow is plotted against temperature. CCC solutions, containing 5, 10 and 15% palmitic acid, were melted first with rising temperature and the crystallization thermodynamic properties followed upon cooling. Based on the results in FIG. 9, significant crystallization did not happen until the concentration of C16 fatty acid approached 15%. These crystals will not only add beauty to the formula, but may also further stabilize the foam resulting in a "Pickering foam", that is, foam stabilized by particulates adsorbed at the air/water interface.

What is claimed is:

1. An aqueous composition comprising
   a) surfactants comprising a salt of a $C_{10-16}$ alcohol ethoxylate sulfate, a betaine surfactant, and an alkyl polyglucoside, wherein the salt of the $C_{10-16}$ alcohol ethoxylate sulfate is present in a quantity that is greater than any other surfactant, and wherein the surfactants comprise, based on a total weight of the surfactants, 60-70 weight % of the salt of the $C_{10-16}$ alcohol ethoxylate sulfate, 20-30 weight % of the betaine surfactant, and 5-15 weight % of the alkyl polyglucoside; and
   b) at least 15 weight % of the composition of a $C_{12-18}$ fatty acid.

2. The composition of claim 1, wherein the surfactants are present in an amount of at least 5 weight % of the composition.

3. The composition of claim 1, wherein the salt of the $C_{10-16}$ alcohol ethoxylate sulfate is sodium lauryl ether sulfate.

4. The composition of claim 1, wherein the salt of the $C_{10-16}$ alcohol ethoxylate sulfate is sodium lauryl ether sulfate with an average of 2 moles of ethylene oxide.

5. The composition of claim 1, wherein the betaine surfactant is cocamidopropyl betaine.

6. The composition of claim 1, wherein the alkyl polyglucoside is decyl glucoside.

7. The composition of claim 1, wherein the surfactants comprise, based on the weight of the surfactants, 66 to 67 weight % of the salt of the $C_{10-16}$ alcohol ethoxylate sulfate, 24 to 25 weight % betaine surfactant, and 9 to 10 weight % alkyl polyglucoside.

8. The composition of claim 1, wherein the $C_{12-18}$ fatty acid is palmitic acid.

* * * * *